United States Patent
Crivello

(10) Patent No.: US 7,405,308 B2
(45) Date of Patent: Jul. 29, 2008

(54) THIANTHRENIUM SALT CATIONIC PHOTOINITIATORS

(75) Inventor: James V. Crivello, Clifton Park, NY (US)

(73) Assignee: Rensselaer Polytechnic Institue, Troy, NY (US)

(*) Notice: Subject to any disclaimer, the term of this patent is extended or adjusted under 35 U.S.C. 154(b) by 102 days.

(21) Appl. No.: 10/990,114

(22) Filed: Nov. 16, 2004

(65) Prior Publication Data

US 2005/0064333 A1  Mar. 24, 2005

Related U.S. Application Data

(63) Continuation of application No. PCT/US03/15622, filed on May 16, 2003.

(60) Provisional application No. 60/380,948, filed on May 16, 2002.

(51) Int. Cl.
C07D 339/08 (2006.01)
C07C 381/12 (2006.01)
C08F 2/50 (2006.01)

(52) U.S. Cl. .......... 549/17; 522/53; 522/904; 522/31; 549/15

(58) Field of Classification Search .......... 522/31, 522/904, 53; 549/15, 17
See application file for complete search history.

(56) References Cited

U.S. PATENT DOCUMENTS

| | | | | |
|---|---|---|---|---|
| 4,069,054 A * | 1/1978 | Smith | | 430/270.1 |
| 4,161,478 A | 7/1979 | Crivello | | 260/327 |
| 4,250,053 A * | 2/1981 | Smith | | 502/167 |
| 5,012,001 A | 4/1991 | Crivello | | 568/13 |
| 5,731,364 A | 3/1998 | Sinta et al. | | 522/31 |
| 6,022,050 A * | 2/2000 | Kline | | 283/81 |
| 6,037,098 A * | 3/2000 | Aoai et al. | | 430/270.1 |
| 6,461,419 B1 * | 10/2002 | Wu et al. | | 106/31.6 |
| 7,230,121 B2 * | 6/2007 | Norcini et al. | | 549/3 |
| 2003/0017415 A1 | 1/2003 | Kodama et al. | | 430/287.1 |
| 2004/0242901 A1 * | 12/2004 | Norcini et al. | | 549/3 |

FOREIGN PATENT DOCUMENTS

| EP | 869393 | 5/2000 |
|---|---|---|
| WO | WO 03/002557 A1 | 1/2003 |
| WO | WO 03/008404 A2 | 1/2003 |

OTHER PUBLICATIONS

C. Selvaraju et al., "Excited State Reactions of Acridinedione Dyes with Onium Salts: Mechanistic Details", Journal of Photochemistry and Photobiology, A: Chemistry, vol. 138, No. 3, 2001, p. 213-226, XP001165619 p. 213, para 1, p. 215, triarylsulphonium salts, (Type III).

Crivello, et al., "Synthesis and Photoactivity of Novel 5-Arylthianthrenium Salt Cationic Photoinitiators", Journal of Polymer Science: Part A: Polymer Chemistry, vol. 40, 3465-3480 (2002).

* cited by examiner

*Primary Examiner*—Susan W Berman
(74) *Attorney, Agent, or Firm*—Heslin Rothenberg Farley & Mesiti P.C.

(57) ABSTRACT

Triarylsulfonium salts of formula I or II are useful as initiators for cationic photopolymerizations:

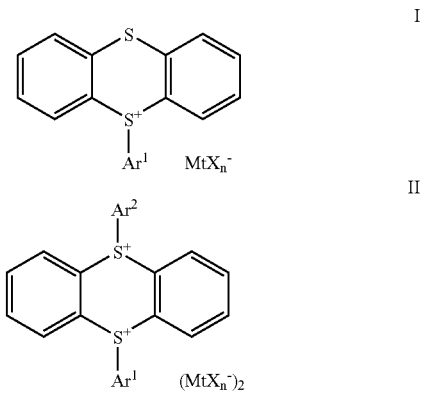

wherein $Ar^1$ and $Ar^2$ are independently polycyclic aryl, substituted aryl, heteroaryl, substituted heteroaryl, or aryl or heteroaryl, pendant from a polymer chain; and $MtX_n^-$ is a complex anion selected from $PF_6^-$, $SbF_6^-$, $AsF_6^-$, $GaF_6^-$, $BF_4^-$, $(C_6F_5)_4B^-$ and $CF_3SO_2)_3C^-$.

4 Claims, No Drawings

THIANTHRENIUM SALT CATIONIC PHOTOINITIATORS

CROSS-REFERENCE TO RELATED APPLICATIONS

This application is a continuation of International Application No. PCT/US03/15622, filed May 16, 2003, which claims priority from U.S. Provisional application Ser. No. 60/380,948, filed May 16, 2002, the entire disclosures of which are incorporated herein by reference.

FIELD OF THE INVENTION

The invention relates to thianthrenium salts, methods for their preparation, and use thereof in cationic photopolymerization processes.

BACKGROUND OF THE INVENTION

Almost twenty-three years ago, Crivello and Lam published the first paper describing the use of triarylsulfonium salts bearing anions of poor nucleophilic character as a novel class of efficient photoinitiators for cationic polymerization. Since this initial paper and due to the significant contributions of many other researchers, the field of photoinitiated cationic polymerization has expanded rapidly. Triarylsulfonium salt cationic photoinitiators are in widespread and increasing commercial use and are currently employed in such applications as printing inks, can and beverage coatings, adhesives, as well as in photo- and stereolithography, among many others.

The most common commercially available triarylsulfonium salt photoinitiators consist of a highly complex mixture of related arylsulfonium salts in which the primary components are shown below.

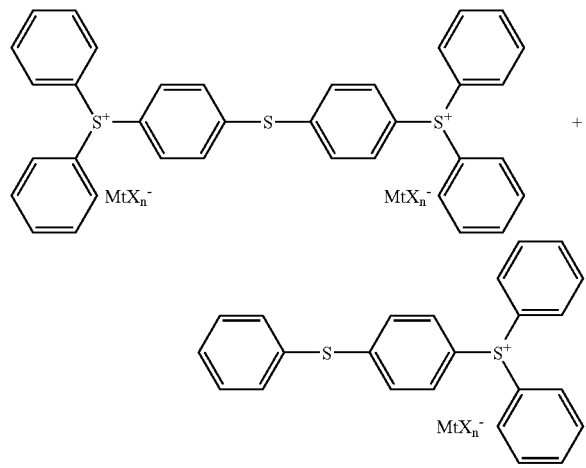

A two-step reaction sequence is used for the synthesis of these materials. In the first step, the condensation of benzene with sulfur monochloride is carried out in the presence of elemental chlorine with aluminum chloride as the catalyst. Thereafter, the resulting mixture of mono- and bissulfonium chlorides are subjected to a metathesis reaction in which the chloride anions are exchanged to provide the active photoinitiator mixture bearing an anion, $MtX_n^-$, of poor nucleophilic character. Typically, $MtX_n^-$ represents a complex anion of the type: $BF_4^-$, $PF_6^-$, $SbF_6^- AsF_6^-$, or, $(C_6F_5)_4B^-$. The ratio of the different salts as well as the many other minor components obtained is largely determined by the stoichiometry of the reactants in the complex condensation reaction shown above as well as by the conditions under which it is carried out. However, in practice, the mixture of sulfonium salts shown above varies substantially from batch to batch and, since the photosenstivities of the triarylsulfonium salts are different, irreproducible and intolerable reactivity variations in many applications are observed. The marginal solubility of these same photoinitiators in many monomers and functional oligomers may also contribute to the irreproducibility of the photosensitivity in some systems. Many nonpolar monomers and functional oligomers fail to polymerize altogether due to the poor solubility of the photoinitiators. Lastly, and most importantly, it has been noted that the UV irradiation of the above photoinitiators results in the formation of benzene as one of the photolysis products. This takes place during the photolysis of the salts chiefly as a result of the homolytic cleavage of the sulfonium salts to form phenyl radicals and their subsequent hydrogen abstraction reactions. Due to the formation of traces of benzene, triarylsulfonium salt photoinitiators have been recently banned from use in Europe in those applications (e.g. printing inks) in which there is the possibility of food contact.

Despite the drawbacks cited above, triarylsulfonium photoinitiators possess many very attractive features that have played a strong role in their acceptance in many commercial applications. They are highly photosensitive and efficiently initiate very rapid vinyl and ring-opening cationic photopolymerizations on UV irradiation. Formulations containing these photoinitiators with monomers have extremely long shelf lives in the absence of UV light. Moreover, mixtures of monomers and triarylsulfonium salt photoinitiators can be heated to temperatures in excess of 120° C. without initiating polymerization. The excellent thermal latency displayed by triarylsulfonium salts is a very desirable property for all practical applications and greatly aids in both the clean up and in the reuse of photosensitive materials. Commercially available sulfonium salt photoinitiators have strong absorption bands in the short wavelength as well as the mid-region (305 nm) of the UV spectrum that is highly desirable since common mercury arc lamps as well as certain laser light sources have prominent emission bands in this region. As a result, many users have optimized their UV irradiation equipment to accommodate the absorption characteristics of these photoinitiators and it would be advantageous to find replacement photoinitiators with the same or a similar UV absorption response. They are nontoxic and have a low incidence of eye and skin irritation. Lastly, the above triarylsulfonium salt photoinitiators are inexpensive and are not easily replaced on a cost basis by other onium salt photoinitiators such as diaryliodonium salts.

The original Crivello paper mentioned above and subsequent papers disclosed 5-phenyl- and 5-(4-methylphenyl)-thianthrenium salts (Crivello, J. V. and Lam, J. H. W., Polymer Journal (Tokyo, Japan) (1985), 17(1), 73-83; Polymer Photochemistry (1982), 2(3), 219-26; and Journal of Polymer Science, Polymer Chemistry Edition (1980), 18(8), 2677-95). In addition, EP 580552, EP 869393, U.S. Pat. No. 5,731,364, U.S. Pat. No. 4,161,478, disclose use of various classes of thianthienium salts as photoinitiators or photoresists. However, problems associated with current photoinitiators were not recognized at that time. WO 03/008404, WO 03/002557 and U.S. 2003/0017415 disclose thianthrenium salts that lie outside the subject matter of the present invention.

There is, therefore, a need for a replacement for the present commercially available triarylsulfonium salt photoinitiators that preserves the same desirable features as triarylsulfonium salt photoinitiators, but avoids the problems outlined above.

SUMMARY OF THE INVENTION

It has been unexpectedly discovered that triarylsulfonium salt photoinitiators formula I or II share desirable features with triarylsulfonium salt photoinitiators, while avoiding many of their disadvantages.

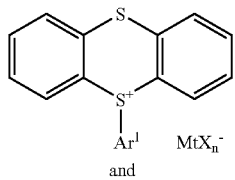

and

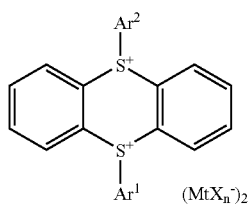

wherein $Ar^1$ and $Ar^2$ are independently polycyclic aryl, substituted aryl, heteroaryl, substituted heteroaryl, or aryl or heteroaryl, pendant from a polymer chain; and $MtX_n^-$ is a complex anion selected from $PF_6^-$, $SbF_6^-$, $AsF_6^-$, $GaF_6^-$, $BF_4^-$, $(C_6F_5)_4B^-$ and $CF_3SO_3^-$, $C_9F_{19}SO_3^-$ and $(CF_3SO_2)_3C^-$.

The thianthrenium salts of this invention closely resemble the commercially available triarylsulfonium salts with respect to their UV absorption characteristics. However, these new photoinitiators have the advantage that their structures may be readily modified to further improve their properties. For example, attachment of a long alkyl or alkoxy group to the aromatic ring produces photoinitiators with improved solubility characteristics. In addition, none of the thianthrenium salt photoinitiators of the present invention generate benzene or other toxic byproducts on exposure to UV radiation.

DETAILED DESCRIPTION OF THE INVENTION

The present invention relates to cationic photopolymerizations using a thianthrenium salt photoinitiator of formula I or II:

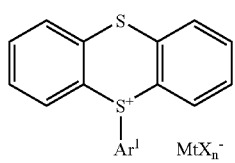

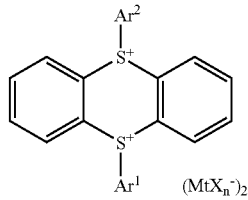

wherein $Ar^1$ and $Ar^2$ are independently polycyclic aryl, substituted aryl, heteroaryl, substituted heteroaryl, or aryl or heteroaryl, pendant from a polymer chain; and $MtX_n^-$ is a complex anion $MtX_n^-$ is an anion of low nucleophilic character selected from $PF_6^-$, $SbF_6^-$, $AsF_6^-$, $GaF_6^-$, $BF_4^-$, $(C_6F_5)_4B^-$ and $CF_3SO_3^-$, $C_9F_{19}SO_3^-$ and $(CF_3SO_2)_3C^-$, with the proviso that $Ar^1$ may not be

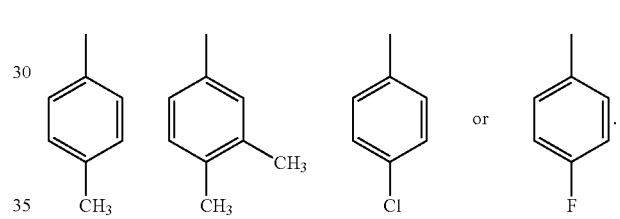

In the context of the present invention, substituted aryl or heteroaryl refers to aryl or heteroaryl wherein up to three H atoms on one or more rings is replaced with alkyl, substituted alkyl, substituted alkynyl, carbonyl, nitro, halogen, haloalkyl, hydroxy, alkoxy, $OCH(COOH)_2$, cyano, primary amino, secondary amino, acylamino, phenyl, benzyl, benzyloxy, heteroaryl, or heteroaryloxy.

Preferred substituents for substituted aryl include lower alkyl, such as methyl; $C_6$-$C_{20}$ alkyl, such as t-butyl, and dodecyl; aryl, such as phenyl, and including residues derivable from fused ring systems, such as naphthalene, a substituted benzene, naphthalene, anthracene, pyrene, perylene, phenanthrene, stilbene or other condensed polynuclear hydrocarbon group. and from ring assemblies, such as biphenyl; heteroaryl, such as benzothiophene, dibenzofuran, thianthrene, dibenzothiophene, thiophene and carbazole; alkoxy, such as methoxy, butoxy, hexyloxy and octyloxy; and aryloxy, except that for substituted aryl, a sole or single substitutent may not be methyl, halo or phenoxy.

In a preferred embodiment, $Ar^1$ and $Ar^2$ are substituted aryl, and substituent groups are lower alkyl, $C_6$-$C_{20}$ alkyl, aryl, alkoxy or aryloxy. Even more preferred substituent groups are methoxy, ethoxy, hexyloxy, octyloxy, methyl, phenyl and phenoxy.

In another embodiment, the invention is directed to compositions containing thianthrenium salt photoinitiators having the structure of I or II in which as defined above. This invention is also directed towards methods used to make these compositions.

Examples of thianthrenium salts of formula I or I include
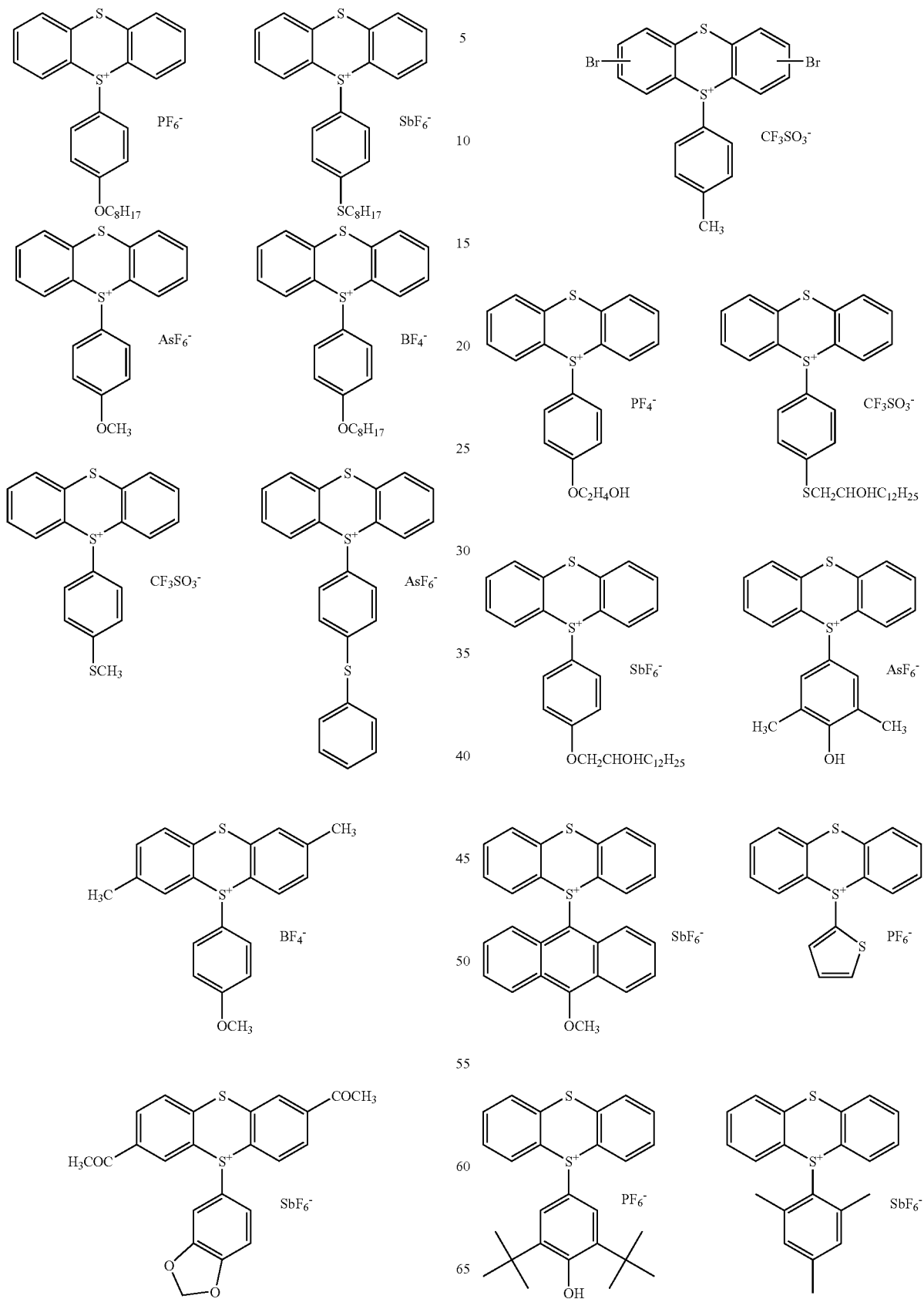

-continued

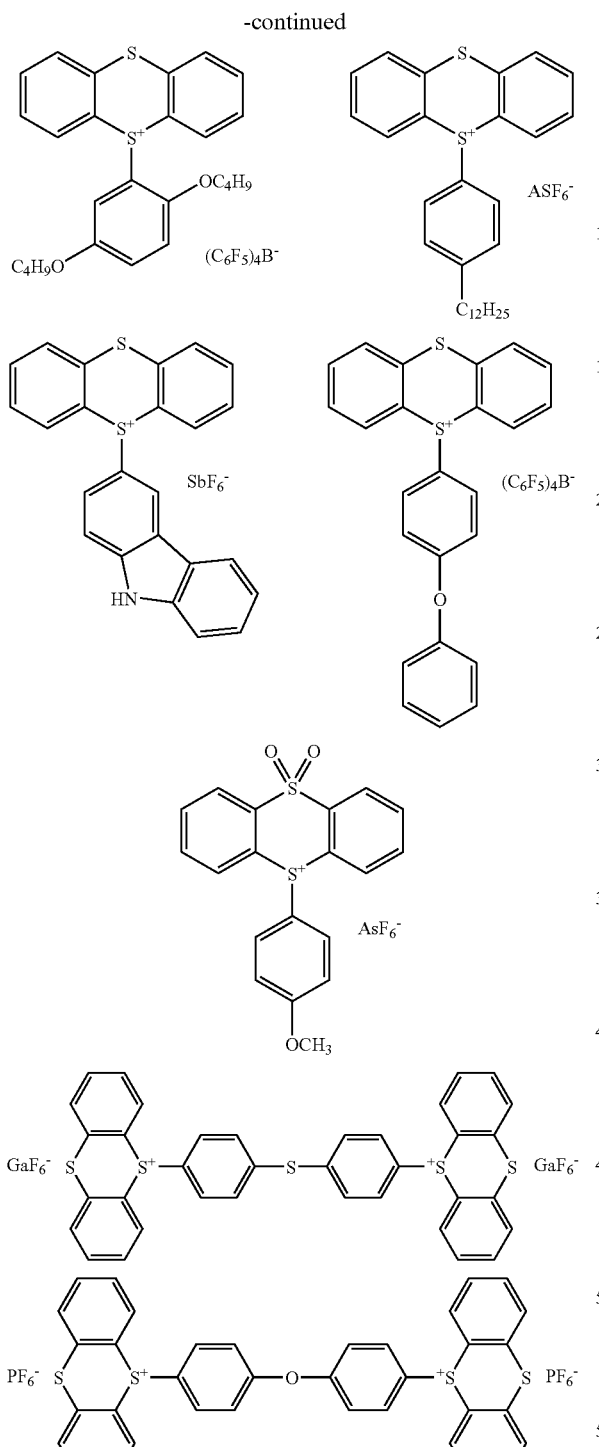
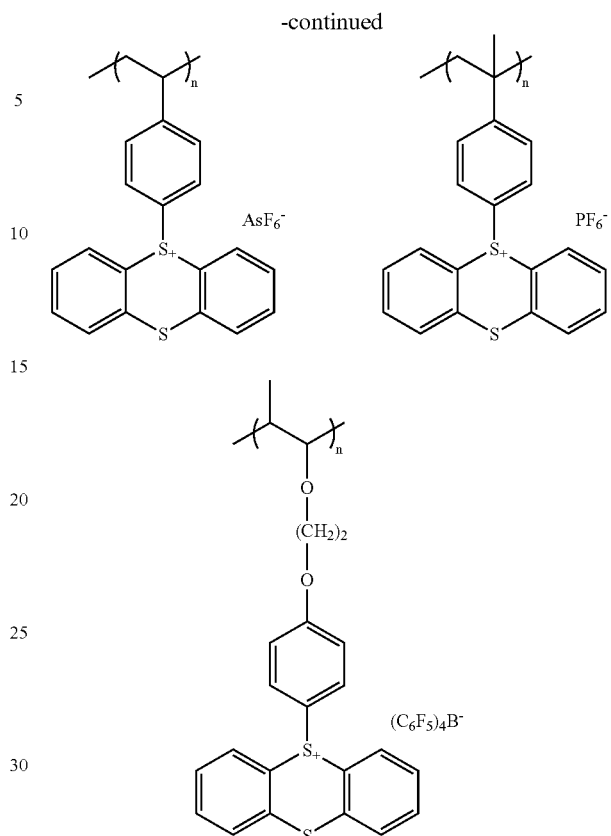

Preferred thianthrenium salts include 5-(4-methoxyphenyl) thianthrenium hexafluorophosphate, 5-(4-methoxyphenyl) thianthrenium hexafluoroantimonate, 5-(4-n-hexyloxyphenyl) thianthrenium hexafluorophosphate, 5-(4-methylphenyl) thianthrenium hexafluorophosphate, 5-(2,5-dimethylphenyl) thianthrenium hexafluorogalate, 5-(2,5-dimethylphenyl) thianthrenium noniflate, 5-(2,4,6-trimethylphenyl) thianthrenium hexafluorophosphate, 5-(2,4,6-trimethylphenyl) thianthrenium tetrakispentafluorophenylborate, 5-(2,4,6-trimethylphenyl) thianthrenium hexafluoroantimonate, 5-(2,4,6-trimethylphenyl) thianthrenium trifluoromethanesulfonate, 5-(4-phenoxyphenyl) thianthrenium tetrafluoroborate, and 5-(4-biphenyl) thianthrenium hexafluoroarsenate.

Accordingly, cationically photopolymerizable compositions of the present invention include the thianthrenium salt photoinitiator described above and one or more cationically photopolymerizable monomers. Typically, the photoinitiator is employed in concentrations ranging from 0.01 to 1.0 mol % based on monomer, or 0.1 to 10% by weight based on the total monomer weight.

Cationically photopolymerizable monomers are known in the art and include mono-, di- and multifunctional epoxides, oxetanes and vinyl ethers. Other monomers that may be used include aziridines, azetidenes, propenyl ethers, allenic ethers, ketene acetals, tetrahydrofuran, ε-caprolactone, β-propriolactone, styrene, α-methyl styrene, indene, benzofuran, acenaphthalene, isobutylene, and isoprene. Of greatest importance as monomers are epoxides, oxetanes and vinyl ethers.

Examples of epoxides that may be used in the compositions of the present invention include cycloaliphatic epoxy resins such as 3,4-epoxycyclohexyl 3',4'-epoxycyclohexane carboxylate (EECH or ERL-4221), bis-(3,4-epoxycyclohexyl) adipate, 4-vinylcyclohexene dioxide (VCHDO), limonene dioxide (LDO), and dicyclopentadiene dioxide; α-olefin epoxides such as 1,2-epoxytetradecane, 1,2-epoxydecane, 1,2-epoxydodecane; glycidyl ethers including bisphenol-A diglycidyl ether (BPADGE), bisphenol-F diglycidyl ether, their extended chain analogs, and 1,4-butanediol diglycidyl ether; brominated epoxy resins such as diglycidyl ethers of tetrabromo-bisphenol-A; epoxy cresol novolacs; epoxy phenol novolacs; epoxidized vegetable oils such as epoxidized soybean oil and epoxidized linseed oil; and glycidyl ester resins, as for example, diglycidyl phthalate. The above listed epoxy resins may be included alone or combined to make epoxy mixtures for use in cationically photopolymerizable compositions. In particular, 4-vinylcyclohexene dioxide, limonene dioxide, 3,4-epoxycyclohexyl 3',4'-epoxycyclohexane carboxylate, epoxidized butadiene and epoxidized vegetable oils, such as soybean and linseed oils, or mixtures thereof, may be used.

Examples of oxetane monomers for use in the present invention are (3-ethyl-3-oxetanylmethyl) phenyl ether (POX) and bis (3-ethyl-3-oxetanylmethyl) ether (DOX). Examples of vinyl ethers are triethylene glycol divinyl ether (DVE-3) and 1,4-cyclohexyldimethyl divinyl ether.

Such monomers may be used alone or in combination with a wide assortment of additives and modifiers. For example, such additives may consist of organic and inorganic fillers, fibers flatting agents, surface-active agents, dyes, pigments and photosensitizers. Low and high molecular weight reactive and unreactive oligomers, and polymers can be added.

The cationically photopolymerizable compositions may also include a photosensitizer. Examples of applicable photosensitizers include polynuclear hydrocarbons such as anthracene, 2-ethoxy-9,10-diphenylanthracene, phenanthrene, pyrene, pyrene-1-methanol, pyrene-3-methanol, anthracene-1-methanol, perylene, perylene-3-methanol, 1,4-diphenylbutadyne, carbazole, N-vinylcarbazole, N-ethylcarbazole, poly-N-vinylcarbazole, phenothiazine, 1 0-ethylphenothiazine, 10-decylphenothiazine, 10-decylphenothiazine-9-dioxide, N-ethylphenothiazine, N-phenylphenothiazine, and N-decylphenothiazine-5,5-dioxide.

Irradiation can be carried out using a wide variety of lamp sources including mercury arc lamps, xenon lamps, quartz halogen lamps that emit in the UV and visible region of the spectrum. Lasers and light-emitting diodes can also be employed for this purpose. With the use of photosensitizers, the photoinitiators of this invention can be used with visible light sources such as incandescent bulbs, spotlights and ambient sunlight to effect polymerizations of the appropriate monomers. In addition, exposure of these same monomers containing the subject photoinitiators to e-beam, γ-ray or x-ray sources of ionizing radiation will also result in their polymerization.

As mentioned previously, formulations containing the subject photoinitiators are useful as UV and radiation curable coatings, printing inks and adhesives. In addition, they are attractive for use in the construction of three-dimensional articles by photopolymerization by a process called stereolithography. They may be additionally employed as the photoactive components of photoresists for the fabrication of integrated circuits and printed wiring boards. The photoinitiators may be used in formulations designed for holographic recording media. They may have many uses in optoelectronic applications including, optical path adhesives, potting and encapsulating resins, fiber-optic coatings and optical waveguides. The thianthrenium salt photoinitiators are also useful for the fabrication of fiber-reinforced composites that are curable either by light or through the use of ionizing radiation. In combination with pendant epoxide-functionalized polydimethylsiloxanes, they may be used in formulations intended for paper release applications or for pressure sensitive adhesives.

The present invention also relates to compositions of thianthrenium salt photoinitiators having the structure of formula I or II.

In another aspect, the present invention relates to a process for preparing a 5-aryl thianthrenium salt. The process includes combining thianthrene-5-oxide with an aromatic compound of formula $Ar^{1A}H$ in the presence of Eaton's reagent, where $Ar^{1A}$ is an electron-rich aromatic substrate selected from aryl, substituted aryl, heteroaryl, substituted heteroaryl, polycyclic aryl or aryl or heteroaryl, pendant from a polymer chain. A methanesulfonate salt of a 5-aryl thianthrenium ion of formula 1A is formed.

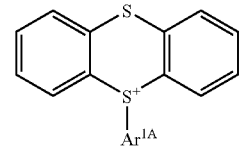

IA

The methanesulfonate salt of the 5-aryl-thianthrenium ion of formula IA is then combined with an alkaline or alkaline earth salt containing an $MtX_n^-$ anion, to form the $MtX_n^-$ salt of a 5-aryl-thianthreni ion of formula IA.

In the method for synthesizing the compounds and/or compositions, thianthrene is directly oxidized with dilute nitric acid to the corresponding thianthrene-5-oxide in nearly quantitative yield.

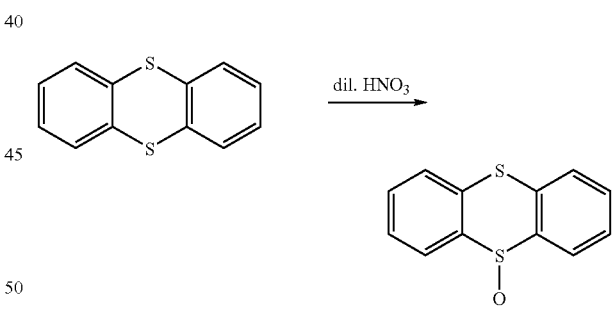

The above reaction provides a very simple and inexpensive means of preparing thianthrene-5-oxide. In a second step, diarylsulfoxides are condensed with electron-rich aromatic compounds to directly form triarylsulfonium salts in high yields. The electron-rich aromatic compounds are compounds that are typically substituted with an electron donating group. An electron donating group is a group that can donate electrons to or share electrons with aromatic or heteroaromatic ring(s) to which they are attached. Examples include monovalent groups, such as alkoxy, especially methoxy, hydroxy; aryl, especially phenyl; and alkyl, especially methyl, as well as divalent groups, such as —OCH$_2$O—. Where the electron donating group(s) is divalent, the ring system is substituted in two positions with the divalent group. In some cases, the electron donating groups may be present on a ring along with electron withdrawing or electronically inactive substitutents, such as nitro, cyano, halo, sulfonate, or carboxylate.

A mixture of methanesulfonic acid (MSA) and phosphorous pentoxide is used respectively, as the catalyst and dehydrating agent.

$$Ar_2S\text{—}O \quad + \quad Ar'H \quad \xrightarrow{\text{MSA}, P_2O_5} \quad Ar_2S^+\text{—}Ar' \quad CH_3SO_3^-$$

This reaction has not been applied to thianthrene-5-oxide.

This reaction can be carried out employing thianthrene-5-oxide and an electron-rich aromatic substrate. One example is shown below.

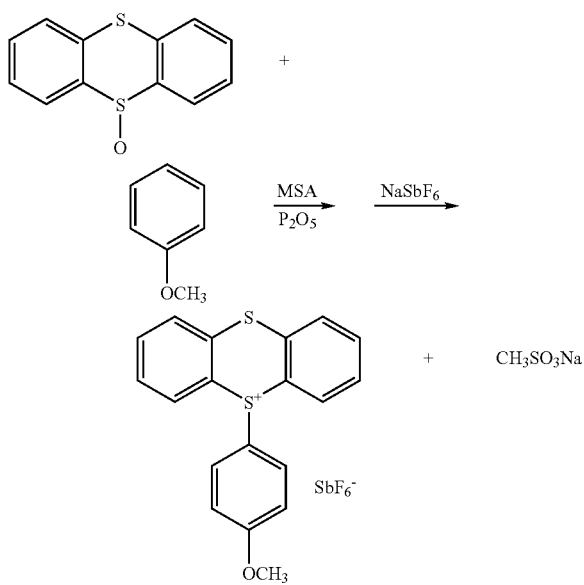

After condensation using MSA/P$_2$O$_5$, the methanesulfonate anion is exchanged with NaSbF$_6$ to provide the active photoinitiator. The product, 4-methoxyphenylthianthrenium hexafluoroantimonate, was obtained as a crystalline solid. Details of the synthesis are given in the experimental portion of this document.

While MSA/P$_2$O$_5$ was used as a combination catalyst/dehydrating agent of choice in this example, other reagents may be employed instead. For example, the combination of acetic anhydride/sulfuric acid or polyphosphoric acid can also be used. The agent used in this reaction will depend on the specific thianthrenium salt desired.

DEFINITIONS

In the context of the present invention, alkyl is intended to include linear, branched, or cyclic hydrocarbon structures and combinations thereof. Lower alkyl refers to alkyl groups of from 1 to 4 carbon atoms. Lower alkyl groups include methyl, ethyl, n-propyl, isopropyl, and n-, s- and t-butyl. Higher alkyl refers to alkyl groups of greater than 5 carbon atoms, preferably 5 to 20 carbon atoms. Preferred alkyl groups are those of C$_{20}$ or below. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl Aryl and heteroaryl mean 5- or 6-membered monocyclic ring structures, as well as polycyclic aryl and polycyclic heteroaryl. Polycyclic aryl groups are those derived from polycyclic aromatic hydrocarbons (PAH), and particularly, fused systems (fused carbocycles) as defined by the Chemical Abstracts Index Guide, 1997 edition, that is, having at least two rings of five or more members and containing only "ortho" or "ortho- and peri-" fusions. Examples of these include, but are not limited to, naphthalene, fluorene, phenanthrene, anthracene, pyrene and perylene. Likewise, polycyclic heteroaryl groups are those derived from polycyclic heteroaromatic compounds, particularly, fused systems (fused heterocycles), containing 0-3 heteroatoms selected from nitrogen, oxygen or sulfur, such as carbazole, phenothiazine, and thianthrene. Aromatic 6- to 14-membered carbocyclic rings include, for example, benzene, naphthalene, indane, tetralin, and fluorene; and 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an alkyl residue attached to an aryl ring. Examples are benzyl and phenethyl. Heteroarylalkyl means an alkyl residue attached to a heteroaryl ring. Examples include pyridinylmethyl and pyrimidinylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, cycloalkyl, or heterocyclyl refer to alkyl, cycloalkyl, or heterocyclyl wherein up to three H atoms in each residue are replaced with halogen, haloalkyl, hydroxy, lower alkoxy, carboxy, carboxalkoxy, carboxamido, cyano, carbonyl, nitro, primary amino, secondary amino, alkylthio, sulfoxide, sulfone, acylamino, acyloxy, amidino, phenyl, benzyl, heteroaryl, phenoxy, benzyloxy, heteroaryloxy, or substituted phenyl, benzyl, heteroaryl, phenoxy, benzyloxy, or heteroaryloxy.

Substituted aryl or heteroaryl refers to aryl or heteroaryl wherein up to three H atoms on one or more rings is replaced with alkyl, substituted alkyl, substituted alkynyl, carbonyl, nitro, halogen, haloalkyl, hydroxy, alkoxy, OCH(COOH)$_2$, cyano, primary amino, secondary amino, acylamino, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

EXAMPLES

Materials and Apparatus

All the organic compounds, reagents and starting materials used in this investigation were purchased from the Aldrich Chemical Company and used without purification unless otherwise noted. Cyclohexene oxide was stirred over calcium hydride and then distilled from calcium hydride prior to use. (3-Ethyl-3-oxetanylmethyl) phenyl ether (POX) and bis (3-ethyl-3-oxetanylmethyl) ether (DOX) were kindly provided by the Toagosei Chemical Co., (Nagoya, Japan). Triethylene glycol divinyl ether (DVE-3) was a gift of the International Specialties Corp. (Wayne, N.J.). 3,4-Epoxycyclohexylmethyl 3', 4'-epoxycyclohexane carboxylate (ERL-4221E) was purchased from the Union Carbide Corp. (Bound Brook, N.J.). S,S-diphenyl-S-(4-thiophenoxyphenyl)sulfonium hexafluoroantimonate was prepared using the method of Crivello (Crivello, J. V.; Varlemann, U. *J. Polym. Sci., Polym. Chem. Ed.* 1995, 33, 2463). The UV absorption spectra were measured in methanol using a Perkin-Elmer Lambda 2 UV-Vis Spectrometer. Melting points were taken on a Thomas-Hoover Capillary Melting Point Apparatus and are uncorrected. UV spectra were recorded on a Perkin-Elmer Lambda 2 UV/Vis Spectrometer. $^1H$- and $^{13}C$ NMR spectra were obtained using a Varian XL 500 MHz spectrometer at room temperature in $CDCl_3$. Elemental analyses were performed by Quantitative Microanalysis, Norcross, Ga.

Synthesis of Thianthrenium Salts

The following description of the preparation of 5-(4-methoxyphenyl) thianthrenium hexafluoroantimonate is illustrative of the synthetic method that was employed for all the thianthrenium salts shown in Table 1.

Example 1

Preparation of Thianthrene-5-Oxide

Thianthrene-5-oxide was prepared using the published method of Gilman and Swayampati using dilute nitric acid as the oxidizing agent. There were obtained a 96% yield of the desired thianthrene-5-oxide having a melting point of 143-144° C. (lit. m.p.[6] 143-143.5° C.).

Example 2

Synthesis of 5-(4-Methoxyphenyl) thianthrenium Hexafluoroantimonate

Into a 125 mL Erlenmeyer flask equipped with a magnetic stirrer and thermometer were placed 10.8 g (0.05 mol) of thianthrene-5-oxide and 11.7 g (0.05 mol) of anisole. To this mixture were added 20 mL of Eaton's reagent (a 1:10 solution of phosphorous pentoxide in methanesulfonic acid). Upon stirring, the reaction mixture became deep blue in color and the temperature spontaneously rose to 40° C. Once the reaction had subsided, the reaction mixture was stirred for an additional 1 h and then poured into 200 mL distilled water. To this mixture with stirring were added 9.2 g (0.05 mol) potassium hexafluorophosphate. Immediate precipitation of the product took place to give a light brown oil that solidified to a beige colored solid. The product was extracted with diethyl ether to remove the dark reaction byproducts. Then, the remaining tan solid was recrystallized from methanol to give a very pale yellow needlelike crystalline product, mp 150-151° C. There were obtained 18.3 g (75.3% of the desired thianthrenium salt product.

Kinetic Studies by Fourier Transform Real-Time IR Spectroscopy (FT-RTIR)

The kinetics of the cationic photopolymerizations of various epoxy and vinyl ether monomers studied during this investigation were monitored using FT-RTIR spectroscopy. The configuration of the apparatus that we have used in our experiments has been described previously. A Midac M-1300 FT-IR spectrometer equipped with a liquid nitrogen-cooled mercury-cadmium-telluride detector was fitted with a UVEX Model SCU-110 mercury lamp in which the light is carried through a flexible wand to the sample compartment. The end of the wand was placed at a predetermined distance and directed at an incident angle of 45° onto the sample window. The intensity of UV irradiation was measured with a UV Process Supply Inc Control Cure Radiometer. All kinetic experiments in this investigation were conducted at 25° C. at such light intensities as to permit a convenient analysis of the data.

Samples for kinetic analysis were prepared as follows: homogeneous solutions of the desired monomer with the designated photoinitiator were prepared (all concentrations are given in mol % with respect to the monomer unless otherwise noted). The solutions were spread as thin films between two layers of 12 μm corona treated oriented polypropylene film and then mounted in 2 cm×2 cm plastic slide holders. The reproducibility of the thickness of various samples was checked by monitoring the peak-to-peak distance taken by the interferometer. During the photopolymerization, a characteristic infrared absorption band of the functional group undergoing polymerization was monitored. The bands that were selected for each of the monomers used are given in Table 2. Data were collected at a rate of one spectrum per second. Then, the spectral data were plotted as conversion versus time curves using Midac Grams/386 software.

Differential Scanning Calorimetric Studies of the Thermal Stability of 5-Aryl-thianthrenium Salt Photoinitiators Differential scanning calorimetric (DSC) studies of the thermal stability of 5-arylthianthrenium salts were carried out with the aid of a Perkin Elmer DSC-7 Differential Scanning Calorimeter. Measurements were carried out by heating solutions of 3,4-epoxycyclohexylmethyl 3',4'-epoxycyclohexane-carboxylate containing 1.0 mol. % 5-(4-methoxyphenyl) thianthrenium salts in air at a heating rate of 5° C./minute. The onset of the exothermic polymerization of the epoxide monomer served as a probe for the practical limit of the thermal stability of the photoinitiator.

RESULTS AND DISCUSSION

Synthesis of 5-Arylthianthrenium Salt Photoinitiators

Gilman and Swayampati have reported that thianthrene undergoes direct oxidization with dilute nitric acid to the corresponding thianthrene-5-oxide in nearly quantitative yield. We have repeated this reaction in our laboratory and have confirmed their previously reported high yield (95-98%).

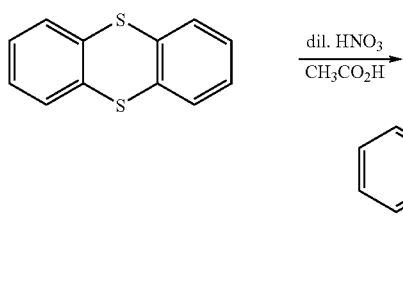

The above reaction provides a very simple, facile and inexpensive means of preparing thianthrene-5-oxide. The resulting diarylsulfoxides undergo smooth condensation with electron-rich aromatic compounds in the presence of a 10:1 mixture of methanesulfonic acid (MSA) and phosphorous pentoxide (Eaton's reagent) to directly form triarylsulfonium salts in high yields.

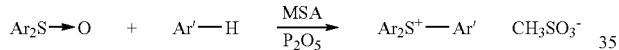

Metathesis of the resulting triarylsulfonium mesylates (methanesulfonates) with an appropriate alkaline or alkaline earth salt containing a $MtX_n^-$ anion gives the desired active triarylsulfonium salt photoinitiators. This reaction scheme had not been applied to thianthrene-5-oxide.

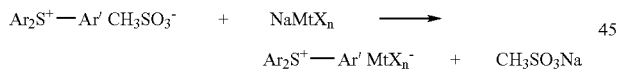

Indeed, when this reaction was carried out employing thianthrene-5-oxide together with a number of aromatic substrates bearing electron-donating groups, the corresponding 5-aryl-substituted thianthrenium salts were obtained in good to excellent yields. An example of this reaction is shown in Scheme 2.

Scheme 2

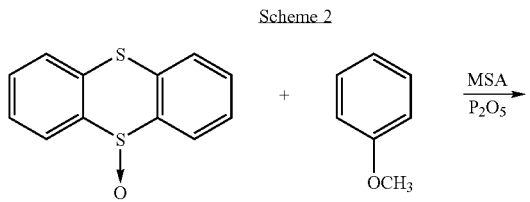

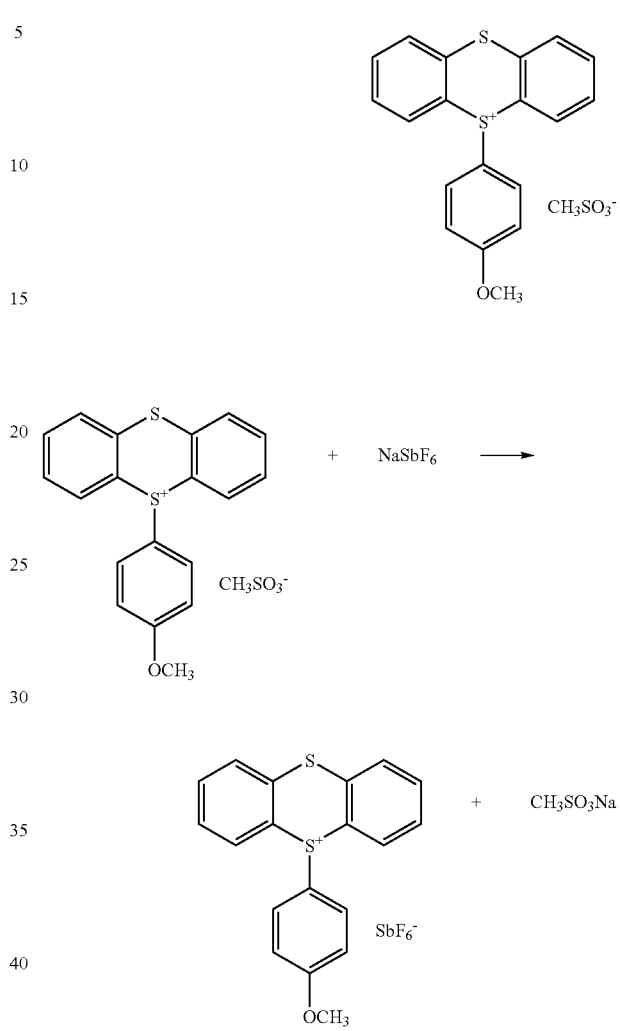

Like many electrophilic substitution reactions, the first step of Scheme 2 is exothermic. After condensation using MSA/$P_2O_5$, the initially obtained mesylate anion ($CH_3SO_3^-$) of the thianthrenium salt was readily replaced with various other non-nucleophilic anions by metathesis in water to afford a series of cationic photoinitiator salts. The 5-arylthianthrenium salts were obtained as colorless to pale yellow or beige solids after purification by recrystallization. When monosubstituted substrates were used, the isolated products bear the substituent on the aromatic ring in the 4-position. Undoubtedly, the formation of minor amounts of the 2-substituted isomer also takes place. However, these latter isomers appear to be less crystalline and to be removed during workup and purification by recrystallization.

Table 1 gives the structures, melting points, yields, and results of the elemental analyses for each of the 5-arylthianthrenium salts prepared during the course of this work. None of the reactions used for the preparation of the 5-arylthianthrenium salts were optimized.

TABLE 1

Structures and Characteristics of Thianthrenium Salt Photoinitiators

| Notation | Structure Ar | MtX$_n$- | MW (g/mol) | m.p. (° C.) | Yield (%) | Elemental Analysis | | |
|---|---|---|---|---|---|---|---|---|
| | | | | | | | % C | % H |
| 1 | 4-MeO-C$_6$H$_4$- | SbF$_6$- | 559.2 | 190–192 | 54 | Calc: | 40.81 | 2.70 |
| | | | | | | Found: | 40.81 | 2.71 |
| 2 | 4-MeO-C$_6$H$_4$- | PF$_6$- | 468.6 | 150–151 | 75 | Calc: | 48.66 | 3.30 |
| | | | | | | Found: | 48.51 | 3.22 |
| 3 | 4-EtO-C$_6$H$_4$- | SbF$_6$- | 573.2 | 159–162 | 24 | Calc: | 41.91 | 2.99 |
| | | | | | | Found: | 42.02 | 3.01 |
| 4 | 4-C$_6$H$_{13}$O-C$_6$H$_4$- | PF$_6$- | 538.6 | 142–144 | 69 | Calc: | 53.52 | 4.68 |
| | | | | | | Found: | 53.34 | 4.82 |
| 5 | 4-C$_8$H$_{17}$O-C$_6$H$_4$- | SbF$_6$- | 657.4 | 83–87 | 65 | Calc: | 47.50 | 4.45 |
| | | | | | | Found: | 47.45 | 4.68 |
| 6 | 2,4-(CH$_3$)$_2$-C$_6$H$_3$- | SbF$_6$- | 557.2 | 107–109 | 89 | Calc: | 43.11 | 3.08 |
| | | | | | | Found: | 43.01 | 3.38 |

TABLE 1-continued

Structures and Characteristics of Thianthrenium Salt Photoinitiators

| Notation | Structure Ar | $MtX_n-$ | MW (g/mol) | m.p. (° C.) | Yield (%) | Elemental Analysis | | |
|---|---|---|---|---|---|---|---|---|
| | | | | | | | % C | % H |
| 7 | 2,4-dimethylphenyl | $PF_6-$ | 466.5 | 195–197 | 82 | Calc: Found: | 51.50 51.71 | 3.67 3.71 |
| 8 | 2,4,6-trimethylphenyl | $SbF_6-$ | 571.3 | 231–233 | 91 | Calc: Found: | 44.15 44.16 | 3.35 3.35 |
| 9 | 2,4,6-trimethylphenyl | $PF_6-$ | 480.5 | 187–188 | 95 | Calc: Found: | 52.50 52.45 | 3.99 4.25 |
| 10 | 2,4,6-trimethylphenyl | $AsF_6-$ | 524.4 | 204–206 | 86 | Calc: Found: | 48.12 48.08 | 3.65 3.63 |
| 11 | 2,4,6-trimethylphenyl | $BF_4-$ | 422.3 | 200–202 | 81 | Calc: Found: | 59.72 59.50 | 4.53 4.96 |
| 12 | 2,4,6-trimethylphenyl | $(C_6F_5)_4B-$ | 1030.6 | 197–198 | 94 | Calc: Found: | 53.61 53.01 | 2.25 1.94 |

TABLE 1-continued

Structures and Characteristics of Thianthrenium Salt Photoinitiators

| Notation | Structure Ar | MtX$_n$– | MW (g/mol) | m.p. (° C.) | Yield (%) | Elemental Analysis | % C | % H |
|---|---|---|---|---|---|---|---|---|
| 13 | 4-(phenoxy)phenyl | PF$_6$– | 530.5 | 155–157 | 100 | Calc: Found: | 54.34 54.46 | 3.23 3.28 |
| 14 | 4-(phenoxy)phenyl | SbF$_6$– | 521.3 | 120–122 | 90 | Calc: Found: | 46.40 47.83 | 2.76 2.87 |
| 15 | 4-biphenyl | SbF$_6$– | 605.3 | 190–191 | 82 | Calc: Found: | 47.62 47.83 | 2.83 2.81 |

TABLE 2

IR Bands Monitored During FT-RTIR Kinetic Studies*

| Monomer | CHO | VCDO | LDO | PC-1000 | POX | DOX | CEVE | DVE-3 |
|---|---|---|---|---|---|---|---|---|
| IR Band (cm$^{-1}$) | 781 | 818 | 800 | 886 | 692 | 829 | 1620 | 1620 |

*CHO, cyclohexene oxide; VCDO, 4-vinylcyclohexene dioxide; LDO, limonene dioxide, PC-1000, 1,3-bis(3,4-epoxycyclohexyl-2-ethyl)-1,1,3,3-tetramethyldisiloxane; POX, (3-ethyl-3-oxetanylmethyl) phenyl ether; DOX, bis(3-ethyl-3-oxetanylmethyl)-ether; CEVE, 2-chloroethyl vinyl ether; DVE-3, triethyleneglycol divinyl ether.

Similarly, in Table 3 are tabulated the UV absorption characteristics and the $^1$H- and $^{13}$C-NMR spectral data for these compounds. UV spectra of arylthianthrenium salts show that the salts have broad absorption throughout the short and middle regions of the UV spectrum. Major aromatic absorption bands are observed in the 240-270 nm region and a longer absorption maximum generally occurs at 290-310 nm. In particular, there is a long wavelength tail that in many cases extends out to approximately 340 nm. For this reason, these photoinitiators display quite excellent photoresponse to common UV emission sources, such as medium pressure mercury arc lamps. It should be noted that the position of the $\lambda_{max}$ is little affected by the character of the anion. Included also in Table 3 is the UV spectra data for a commercially available triarylsulfonium salt. A comparison of this latter data with the corresponding data for 5-arylthianthrenium salts from Table 3 shows that it possesses similar UV spectral characteristics but that the long wavelength absorption band at 301 nm has a considerably greater molar extinction coefficient ($\epsilon=21,300$).

TABLE 3

UV Spectral Data[a] For Triarylsulfonium Salts

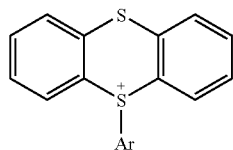

| Ar | Anion | λ (nm) | ε (L/cm mol) |
|---|---|---|---|
| ![p-methoxyphenyl] —C6H4—OCH3 | SbF6− | 201<br>~247[b]<br>309 | 51560<br>17700<br>5880 |
| ![p-methoxyphenyl] —C6H4—OCH3 | PF6− | 202<br>~247[b]<br>309 | 50970<br>17680<br>5850 |
| ![p-ethoxyphenyl] —C6H4—OC2H5 | SbF6− | 202<br>250<br>~310[b] | 54910<br>18390<br>5840 |
| ![p-hexyloxyphenyl] —C6H4—OC6H13 | PF6− | 201<br>249<br>~310[b] | 52290<br>18830<br>5950 |
| ![p-octyloxyphenyl] —C6H4—OC8H17 | SbF6− | 202<br>250<br>~310[b] | 55200<br>19000<br>5710 |

TABLE 3-continued
UV Spectral Data[a] For Triarylsulfonium Salts
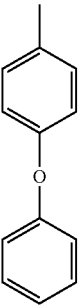
| Ar | Anion | λ (nm) | ε (L/cm mol) |
|---|---|---|---|
| 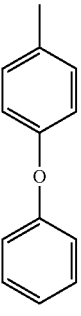 | PF$_6$− | 201<br>253<br>~310[b] | 62870<br>20090<br>5850 |
| 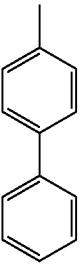 | SbF$_6$− | 202<br>252<br>~309[b] | 56310<br>18570<br>5500 |
| 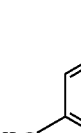 | SbF$_6$− | 202<br>268 | 60490<br>26720 |
|  | SBF$_6$− | 203<br>298 | 52460<br>5490 |
|  | PF$_6$− | 203<br>300 | 52460<br>5510 |

TABLE 3-continued
UV Spectral Data[a] For Triarylsulfonium Salts
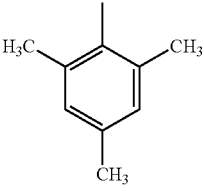
| Ar | Anion | λ (nm) | ε (L/cm mol) |
|---|---|---|---|
| 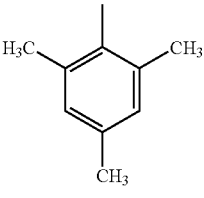 | $SbF_6-$ | 205<br>243<br>292 | 56740<br>23450<br>5900 |
| 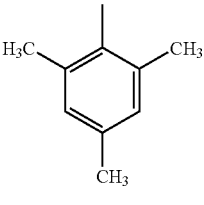 | $BF_4-$ | 203<br>244<br>292 | 55840<br>21780<br>5460 |
| 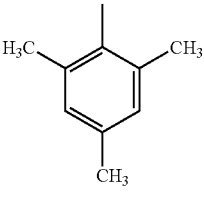 | $B(C_6F_5)-$ | 201<br>~244[b]<br>291 | 82890<br>24220<br>5740 |
| 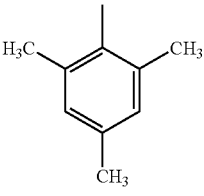 | $PF_6-$ | 205<br>244<br>291 | 55960<br>22890<br>5800 |
| 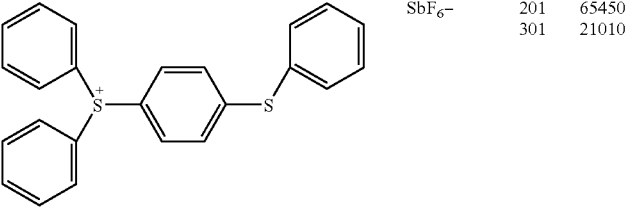 | $AsF_6-$ | 205<br>244<br>292 | 56420<br>22890<br>5700 |
|  | $SbF_6-$ | 201<br>301 | 65450<br>21010 |
[a]Measured in methanol.
[b]Bands in 200 nm region cannot be determined exactly due to competitive solvent absorption.

As may be noted in Table 1, the synthetic procedure we have described in Scheme 2 is a simple, straightforward and high yield method that is suitable for the preparation of a wide variety of 5-arylthianthrenium salts bearing different electron donating substituents on the aryl groups as well as various counterions. Manipulation of the substituents on the aryl rings affords the possibility of tailoring the melting points, solubility and UV absorption characteristics of the respective 5-arylthianthrenium salts. Although these organic salt compounds are analytically pure, they often give broad melting points (typically, a two degree melting point range is observed). Alkoxy-substituted benzenes undergo smooth reaction with thianthrene-5-oxide to form the corresponding 5-(4-alkoxyphenyl) thianthrenium salts (entries 1-5). An increase in the length of the alkoxy chain in these compounds is accompanied by a corresponding increase in solubility and a decrease in their melting points. When the alkoxy chain exceeds eight carbon atoms, the thianthrenium salts were obtained as noncrystallizable oils. While these latter compounds display excellent activity as photoinitiators, their purification is problematic and for this reason, they were not included in Table 1.

The use of various methylated benzenes as substrates in Scheme 1 was investigated. p-Xylene (entries 6,7) and mesitylene (1,3,5-trimethylbenzene) (entries 8-12) give high yields of the desired thianthrenium salts. However, 1,2,4,5-tetramethylbenzene and pentamethylbenzene appear to mainly undergo oxidative side reactions. The reaction of mesitylene with thianthrene-5-oxide is particularly facile and high melting point crystalline photoinitiator salts bearing five different anions were readily prepared in excellent yields. Similarly, 5-(4-phenoxy)phenylthianthrenium hexafluorophosphate (entry 13) and the corresponding hexafluoroantimonate (entry 14) were obtained in high yields by the reaction of phenyl ether with thianthrene-5-oxide. These compounds are highly soluble in a wide range of nonpolar monomers. Biphenyl reacts smoothly with thianthrene-5-oxide to give an excellent yield of the desired high melting 5-(4-phenyl)phenylthianthrenium salt (entry 15).

There are some limitations to the synthetic methods described above. These arise, as mentioned above, primarily when there are oxidizable groups present in one of the substrates. For example, when condensation of thianthrene-5-oxide with thioanisole was attempted, thianthrene was isolated as the primary product. We propose, as shown in equation 8, that thianthrene-5-oxide oxidizes thioanisole to the corresponding sulfoxide. Thioanisole-S-oxide subsequently undergoes a variety of condensation reactions with thioanisole and with thianthrene to give a complex mixture of sulfonium salt products.

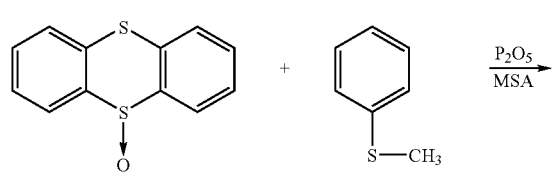

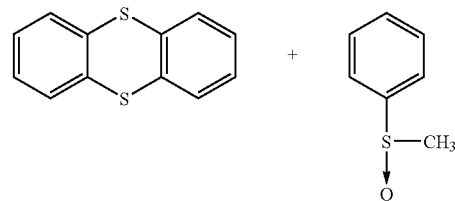

Similarly, the attempted coupling of thianthrene-5-oxide with phenyl sulfide results in the formation of a complex mixture of products resulting from the acid catalyzed condensation of both thiophene-5-oxide and phenylsulfoxide.

Cationic Photopolymerizations

Having prepared, isolated and characterized a new series of 5-arylthianthrenium salts it was of further interest to determine their reactivity as photoinitiators and to compare them with existing related triarylsulfonium salt photoinitiators. Initial screening studies were conducted in which the photoinitiators shown in Table 1 were dissolved in various di- and multifunctional epoxy and vinyl ether monomers and then cast as thin films onto glass plates. Upon irradiation with UV light for a few seconds, the films were converted to nontacky, colorless solids. Based on these preliminary results, a more rigorous study of the behavior of these novel photoinitiators under well-controlled conditions was undertaken. For this purpose, we have employed Fourier transform real-time infrared spectroscopy (FT-RTIR) to monitor the course of the photoinitiated cationic polymerizations under study. Specific details of the technique and the apparatus we have employed in our work are described in the experimental portion of this paper.

Example 3

Photopolymerization of two epoxide monomers, cyclohexene oxide and 4-vinyl cyclohexene dioxide carried out in the presence of a typical thianthrenium salt, 5-(4-methoxyphenyl) thianthrenium hexafluoroantimonate (Table 1, entry 1) was studied by FT-RTIR. The profiles of these two photopolymerizations are indicative of the very good response of these thianthrenium salt photoinitiators to irradiation with broad band UV light. The faster rate and higher conversion in the case of cyclohexene oxide as compared to the polymerization of 4-vinyl cyclohexene dioxide observed here are quite characteristic of difference in behavior between mono- and difunctional monomers in photoinitiated cationic polymerizations. In the case of cyclohexene oxide, the polymerization proceeds rapidly in the initial phases of the polymerization due to the high reactivity of this monomer. However, during the bulk polymerization of the monomer, the polymer formed undergoes a phase transition as solidification takes place. At this point, the rate slows markedly as the $T_g$ of the glassy polymer being formed approaches the reaction temperature. Since 4-vinylcyclohexene dioxide is a highly reactive difunctional monomer, it undergoes the transformation from a liquid to a gelled network polymer at rather low conversions. Moreover, the network that is formed is rigid (high $T_g$) due to the stiffness of the cyclohexane rings and to the short distance between crosslinks. In this case, the rate slows dramatically at this stage of the polymerization and high conversions of the epoxide functional groups cannot be obtained due to their restricted mobility within the three dimensional matrix that is formed.

Example 4

The ring-opening photopolymerizations of mono- (POX) and difunctional (DOX) oxetane monomers were also investigated. In this case, an arylthianthrenium salt bearing an n-octyloxy group in the 4-position of the aromatic ring (Table 1, entry 5) was used to provide solubility in these two monomers. A long induction period followed by rapid polymerization of the two monomers is observed. This behavior has been reported previously for these monomers by Kato and Sasaki and was attributed by them to result from a slow initiation process for the two monomers.

Example 5

Two examples of the photopolymerizations of vinyl ether monomers 2-chloroethyl vinyl ether and triethylene glycol divinyl ether (DVE-3) in the presence of 5-(4-methoxyphenyl) thianthrenium hexafluorophosphate (Table 1, entry 2). The excellent solubility of this initiator in these two nonpolar monomers made it possible to study their photopolymerizations in detail. A long induction period (approx. 45 sec.) in the polymerization of 2-chloroethyl vinyl ether was observed and is due to the presence of a basic polymerization inhibitor that was added to this monomer. In contrast, the commercially available difunctional monomer DVE-3 showed high reactivity and a very short induction period. In the case of this latter difunctional monomer, the conversion is high since the long polyether chain between the two functional groups produces a low $T_g$ crosslinked matrix with a relatively open network structure.

Example 6

Photopolymerization of cyclohexene oxide was carried out in the presence of 0.5 mol % of three structurally different sulfonium salt cationic photoinitiators. In this study, the efficiency of the two thianthrenium salts with triarylsulfonium salt bearing the same (hexafluoroantimonate) anion can be directly compared. The triarylsulfonium salt displays exceptional reactivity in the presence of this monomer. The two 5-arylthianthrenium salts also display excellent but are slightly less efficiency as photoinitiators. Of particular interest in this study is a comparison of triarylsulfonium salt with the analogous 5-(4-methoxyphenyl) thianthrenium hexafluoroantimonate (Table 1, entry 1). The corresponding UV absorption spectra given in Table 3 reveal that while 5-(4-methoxyphenyl) thianthrenium hexafluoroantimonate has similar absorption spectra, 5-(4-biphenyl) thianthrenium hexafluoroantimonate lacks the long wavelength absorption band at 301-310 nm possessed by the other two photoinitiators.

Example 7

Photopolymerization of cyclohexene oxide in the presence of 5-(2,4,6-trimethylphenyl) thianthrenium salts bearing the hexafluoroantimonate and the tetrakis(pentafluorophenyl) borate anion was compared. Very similar rates were noted for photoinitiators containing these two different anions with low nucleophilic character. In a similar study, 5-(2,4,6-trimethylphenyl) thianthrenium salts bearing the $AsF_6^-$, $PF_6^-$ and $BF_4^-$ anions were compared in the photopolymerization of 4-vinylcyclohexene dioxide. The initial rates of polymerizations of this monomer appear to be very similar and independent of the character of the anion. This result is surprising in view of previous results with other onium salts that has indicated polymerization rates decreasing in the order $AsF_6^- > PF_6^- >> BF_4^-$. The reasons for the observations described here are not understood.

Photolysis of 5-Arylthianthrenium Salts

Based on previous mechanistic work on triarylsulfonium salts, it is proposed that under UV irradiation, the photolysis of 5-arylthianthrenium salts proceeds via the abbreviated mechanism shown in Scheme 3 involving the homolysis of one of the three bonds to the positively charged sulfur atom.

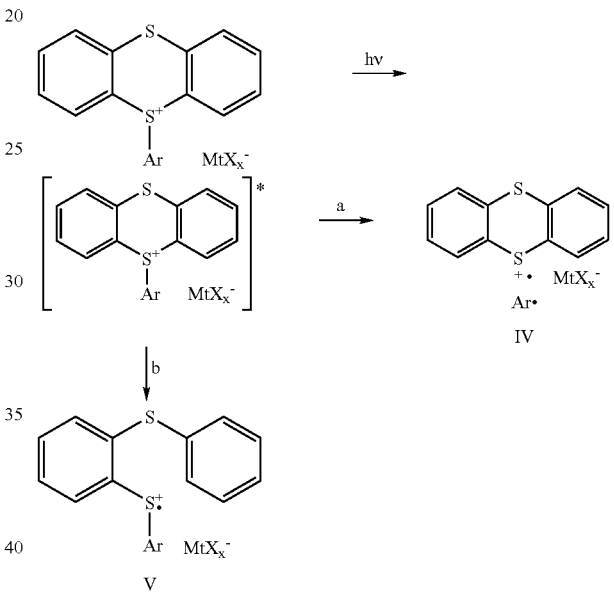

Scheme 3

Photoinduced cleavage can occur via pathway a to generate the thianthrene cation-radical and an aryl radical, IV. In this case, cage escape of this geminate pair leads to the ultimate formation of the strong Bronsted acid, $HMtX_n$, through hydrogen abstraction reactions of the thianthrene cation-radical and also by its reactions with hydroxylic or other protogenic impurities present in the reaction mixture. Alternatively, cleavage of one of the carbon-sulfur bonds of the thianthrene ring (pathway b) yields the cation-radical radical pair, V. This species can further react by a number of subsequent reactions. However, because the geminate pair is held together by the other covalent bonds in the molecule, it can readily collapse back to the starting salt by dissipation of the excitation energy. This is an energy wasting process and would result in a less efficient initiation. Pathway b is not available to non-cyclic triarylsulfonium salts. Thus, the observation that 5-arylthianthrenium salts have slightly lower photoactivity than the related triarylsulfonium salt can be partially explained by the mechanism shown in Scheme 3. However, the more intense longer wavelength (301 nm) absorption of the triarylsulfonium salt as compared to the corresponding 5-arylthianthrenium salts is probably the major contributing factor to the observed difference. Cage recombination of the geminate pair, IV, as shown in equation 9 at other positions on the thianthrene ring can also take place to afford aryl-substituted thianthrenes, VI, with the concomitant release of a proton. This latter proposed mechanism is similar to the one proposed by Saeva et al. for the photolysis of 5-benzylthianthrenium salts.

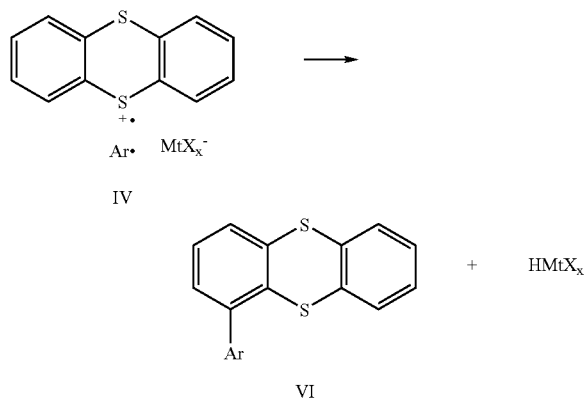

The strong protonic acids released by the photolysis of 5-arylthianthrenium salts are very powerful initiators of cationic polymerization. Preliminary screening studies showed that these onium salts were highly efficient photoinitiators for both vinyl and ring-opening cationic polymerizations.

Example 8

Photosensitization of 5-Arylthianthrenium Salts

As previously mentioned, 5-arylthianthreneium salts have rather strong UV absorption bands at wavelengths from 200-250 nm together with a tail absorption extending out to approximately 330 nm. Thus, while the photosensitivity of these photoinitiators is excellent in the short wavelength region, at longer UV wavelengths they are considerably less sensitive. Furthermore, the 5-arylthianthrenium salts are virtually insensitive to light at visible wavelengths due to their lack of absorption bands in these regions. The use of photosensitizers both increases the overall photoresponse of onium salt photoinitiators to broad band emission sources as well as specifically tailors their absorption to monochromatic light sources.

In the case of onium salt photoinitiators, it has been shown that electron-transfer photosensitization is the most efficient means of spectrally broadening the response of these compounds. Polynuclear aromatic compounds and certain of their derivatives are especially efficient electron-transfer photosensitizers for triarylsulfonium salt photoinitiators. Accordingly, we have undertaken two brief studies to determine whether 5-arylthianthrenium salts can be effectively photosensitized using several common electron-transfer agents. These studies were conducted using broad band UV light. The polymerization of cyclohexene oxide was carried out in the presence and absence of pyrene-1-methanol as a photosensitizer. A large increase in the initial rate of polymerization was found and is indicative of the combined direct photolysis of the 5-arylthianthrenium salts together with an efficient photosensitization of the onium salt by pyrene-1-methanol. It was also reported recently from this laboratory that poly(N-vinylcarbazole) (PVK) is an excellent photosensitizer for a wide variety of onium salt cationic photoinitiators including sulfonium salts. Limonene dioxide was photopolymerized using 5-(2,4-dimethylphenyl) thianthrenium hexafluoroantimonate in the presence of 2 mol % PVK as a photosensitizer. Again, the results indicated that PVK is an efficient photosensitizer for 5-arylthianthrenium salts.

Example 9

Thermal Stability by DSC

The thermal stability of a cationic photoinitiator is of considerable importance since it is highly undesirable for monomers to undergo spontaneous thermally induced polymerization in the absence of light. One method of obtaining an estimation of the latency of a photoinitiator is to determine the temperature of the onset of thermally induced polymerization in a given monomer system by Differential Scanning Calorimetry (DSC). Accordingly, a DSC scan of the commercially important monomer, 3,4-epoxycyclohexylmethyl 3',4'-epoxycyclohexane carboxylate containing 1.0 mol. % 5-(4-methoxyphenyl) thianthrenium hexafluoroantimonate was carried out in air at a heating rate of 5° C./minute. The onset of thermally induced polymerization occurred at approximately 170° C. while the peak of the exotherm was at 220° C. An analogous study using 1 mol % 5-(4-methoxyphenyl) thianthrenium hexafluorophosphate was also carried out. However, in this case, thermally induced polymerization did not occur below 220° C. Therefore, it may be concluded that thianthrenium salts, while paradoxically exhibiting excellent photosensitivity, also show extraordinarily good thermal stability in the absence of light.

CONCLUSIONS

5-Arylthianthrenium salts were conveniently prepared by a straightforward two-step, one-pot reaction sequence in which thianthrene-5-oxide is first treated with an electron-rich aromatic compound in the presence of a mixture of methanesulfonic acid and phosphorous pentoxide as both a catalyst and dehydrating agent. In the second step, the mesylate anion of the resulting thianthrenium salt is then exchanged to give the active photoinitiator. The novel 5-aryl thianthrenium salts were fully characterized by the usual analytical and spectroscopic techniques. These compounds display excellent thermal latency in the presence of various monomer systems and high efficiency as photoinitiators of cationic polymerization. Initial studies demonstrated that these photoinitiators can be readily photosensitized using electron-transfer photosensitizers. The measured onset of thermal initiation in one epoxide monomer was shown to be 220° C. Comparisons of these new photoinitiators with currently commercially employed triarylsulfonium salts showed that for most monomer systems, the new photoinitiators performed similarly with respect to their photosensitivity and ability to rapidly initiate cationic polymerizations under irradiation with UV light.

The invention claimed is:
1. A process for preparing a 5-aryl thianthrenium salt, said process comprising, in the presence of Eaton's reagent, combining thianthrene-5-oxide with an aromatic compound of formula $Ar^{1-4}H$ to form a methanesulfonate salt of a 5-arylthianthrenium ion of formula IA

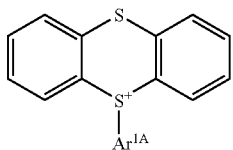

IA wherein $Ar^{1A}$ is aryl, substituted aryl, heteroaryl, substituted heteroaryl, polycyclic aryl, aryl pendant from a polymer chain or heteroaryl pendant from a polymer chain.

2. A process according claim 1, additionally comprising combining the methanesulfonate salt of the 5-aryl-thianthrenium ion with an alkaline or alkaline earth salt containing an $MtX_n^-$ anion, to form an $MtX_n^-$ salt of a 5-aryl-thianthrenium ion of formula IA.

3. A process according to claim 2, additionally comprising preparing thianthrenium-5-oxide by oxidation of thianthrene.

4. A process according to claim 3, wherein thianthrene is oxidized by dilute nitric acid.

* * * * *